(12) United States Patent
Frei et al.

(10) Patent No.: US 6,544,769 B1
(45) Date of Patent: Apr. 8, 2003

(54) COMPOSTIONS COMPRISING VIRUSES AND METHODS FOR CONCENTRATING VIRUS PREPARATIONS

(75) Inventors: Andreas Frei, Freehold, NJ (US); Henry K. H. Kwan, Summit, NJ (US); Varda E. Sandweiss, Forest Hills, NY (US); Gary J. Vellekamp, Glen Ridge, NJ (US); Pui-Ho Yuen, Princeton Junction, NJ (US); Peter Ihnat, Brooklyn, NY (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/249,646

(22) Filed: Feb. 12, 1999

Related U.S. Application Data

(63) Continuation-in-part of application No. 08/989,227, filed on Dec. 11, 1997, now Pat. No. 6,261,823.
(60) Provisional application No. 60/085,559, filed on May 15, 1998, provisional application No. 60/074,873, filed on Feb. 17, 1998, and provisional application No. 60/033,176, filed on Dec. 13, 1996.

(51) Int. Cl.[7] .......................... C12N 7/00; A61K 9/127; A61K 39/395; A01N 37/18
(52) U.S. Cl. ................. 435/235.1; 424/450; 424/184.1; 514/2; 514/937
(58) Field of Search ............................ 424/450, 184.1, 424/204.1, 234.1, 812; 514/2, 937, 938; 435/235.1

(56) References Cited

U.S. PATENT DOCUMENTS

| | | | |
|---|---|---|---|
| 4,569,794 A | | 2/1986 | Smith et al. |
| 5,447,859 A | | 9/1995 | Prussak |
| 5,480,800 A | | 1/1996 | Legoux et al. |
| 5,521,082 A | | 5/1996 | Lewis et al. |
| 5,607,851 A | | 3/1997 | Pellegrini et al. |
| 5,633,230 A | * | 5/1997 | Twist .......................... 514/15 |
| 5,705,378 A | | 1/1998 | Yoshida et al. |
| 5,709,879 A | * | 1/1998 | Barchfeld .................... 424/450 |
| 5,788,965 A | * | 8/1998 | Berkner et al. ........... 424/94.64 |
| 5,837,520 A | | 11/1998 | Shabram et al. |
| 6,227,195 B1 | * | 5/2001 | Gonda ......................... 128/200 |
| 6,261,823 B1 | * | 7/2001 | Tang et al. .................. 210/660 |

FOREIGN PATENT DOCUMENTS

| | | |
|---|---|---|
| BE | 866 330 | 10/1978 |
| DE | 295 927 | 11/1991 |
| DE | 299 213 | 4/1992 |
| EP | 0 302 692 | 8/1988 |
| EP | 0302692 | 2/1989 |
| EP | 0522291 A1 | 1/1993 |
| EP | 0593339 A1 | 4/1994 |
| WO | WO 95/11984 | 5/1995 |
| WO | WO 95/16772 | 6/1995 |
| WO | WO 96/22378 | 7/1996 |
| WO | WO 97/25072 | 7/1997 |
| WO | WO 98/02522 | 1/1998 |
| WO | WO 98/22588 | 5/1998 |

OTHER PUBLICATIONS

Morris–Krsinich et al, "Infection of turnip leaf protoplasts with turnip rosette virus", J. Gen. Virol., vol. 43, part 2, May 1979, pp. 339–347.*
Kanegae, et al. "A simple and efficient method for purification of infectious recombinant adenovirus," Jpn. J. Med. Sci. Biol. (Abstract only) 47 (3): 157–66 (1994).
Tai et al., "The stabilizing effect of various agents in different concentrations on respiratory syncytial," Chin. J. Microbiol., 7/1 (20–24) (1974). (Abstract only).
Huyghe et al., Human Gene Therapy 6:1403–1416 (1995).
Philipson, Virology 10:459–465 (1960).
Philipson, "Chromatography and Membrane Separation," Methods in Virology, (Marmorosch and Koprowski, eds.), 6:179–233 (Academic Press, 1967).
Albrechten et al., J. Virol. Methods 28:245–256 (1990).
Hewish et al., J. Virol. Methods 7:223–228 (1983).
Haruna et al., Virology 13(1):264–267 (1961).
Kanegae et al., Jpn. J. Med. Sci. Biol. 47(3):157–66 (1994) (Abstract only).
Crooks et al., J. Chrom. 502:59–68 (1990).
Mento, S. J. Viagene, Inc., as reported at the 1994 Williamsburg Bioprocessing Conference.
Klemperer et al., Virology 9:536–545 (1959).
Belew et al., Anal. Biochem. 164(2):457–465 (1987).
Kato et al., J. Chrom. 354:511–517 (1986).
Nikolaeva et al., Abstract of S–kh Biol. 10:75–78 (1985).
Hjorth et al., J. Virol. Methods 5:151–158 (1982).
Gekko et al., Biochemistry 20:4677–4686 (1981).
Gekko et al., J. Biochem. 107:572–577 (1990).
Chang et al., "Manual of Industrial Microbiology and Biotechnology," (Demain and Solomon, eds.) pp. 49–55 (1986).
Fukumoto et al., Abstract of Ann. Phytopathol Soc., Jpn. 49(2):220–227 (1983).
Nair et al., Indian Vet. J. 65:183–187 (1988).
Kounounguissa et al., J. Phytopatho. 127:29–41 (1989).
House et al., Journal of Veterinary Diagnostic Investigation 2:44–50 (1990).
Ferris et al., Journal of General Virology 48 (Pt. 2):411–415 (1980).
Abdelmoeti et al., Vaxtskyddsrapporter Avhandlingar 3 (1979).
Gupta et al., Vaccine 14(15):1417–20 (1996).

(List continued on next page.)

Primary Examiner—Mary K. Zeman
Assistant Examiner—Lori A. Clow
(74) Attorney, Agent, or Firm—James M. Gould; David B. Schram; Sandy Zaradic

(57) ABSTRACT

A composition is disclosed comprising virus in a formulation comprising a polyhydroxy hydrocarbon buffered to maintain a pH in a range from about 7 to about 8.5 at a temperature in the range from about 2° C. to 27° C. Methods for concentrating and purifying virus preparations are also disclosed.

5 Claims, No Drawings

OTHER PUBLICATIONS

Franks, "Conformational Stability of Proteins," *Protein Biotechnology*, (F. Franks, ed.) 11:395–436 (The Humana Press, Inc., 1993).

Gherna, "Manual of Methods for General Bacteriology," (Demain and Solomon, eds.) 12:208–217 (1981).

Heckly, *Advances in Applied Microbiology* 24:1–53 (1978).

Hill, Abstract of Proc. Int. Wild Dis. Conf., *Wildlife Diseases*, (Page, ed.), pp. 445–452 (Plenum Press, 1975).

Nyiendo et al., *Appl. Microbiol.* 27(1):72–77 (1974).

Philipson, *Virology* 15:263–268 (1961).

Zeman et al., Microfiltration and Ultrafiltration, vol. II, pp.

Gekko, K. et al., Biochemistry 20, pp. 4677–4686 (1981).

Gekko, K. et al., J. Biochem. 107, pp. 572–577 (1990).

Franks, F., "Conformational Stability of Proteins", Chapter 11 in *Protein Biotechnology* (F. Franks, ed.), pp. 395–436 (Humana Press, 1993).

Chang, L.T. et al., "Manual of Industrial Microbiology and Biotechnology", (Demain, A.L. and N.A. Solomon, eds.), p 466 (1986).

Gherna, R.L., "Manual of Methods for General Bacteriology", pp. 208–271 (1981).

Heckly, R.J., "Advances in Applied Microbiology", vol. 24, pp. 1–53 (1978).

Heckly, R.J. et al., Cryobiology 15, pp. 655–658 (1978).

Fukumoto, et al., BIOSIS Abstract of Ann. Phytopathol. Soc. Jpn. 49 (2) 220 (1983).

Nair, et al., Indian Vet J. 65 (3) 183–187 (1988).

Kounounguissa, et al., J. Phytopathol 127 (1) 29–41 (1989).

House, et al., Journal of Veterinary Diagnostic Investigation on 2 (1) 44–50 (1990).

Ferris, et al., Journal of General Virology 48 (Pt. 2) 411–15 (1980).

Abdelmoeti, et al., Vaextskyddsrapporter, Avh. 3 (Paper No. 3)(1979).

Gupta, et al., Vaccine 14 (15) 1417–20 (1996).

Cunha, et al., Abstract of Rev. Bras. Biol. 37 (2) 345–9 (1977).

Hill, Abstract of Proc. Int. Wildl. Dis. Conf., 445–52 (1975).

Nikolaeva, et al., Abstract of S–kh Biol. (10) 75–78 (1985).

Nyiendo, et al., Appl. Microbiol. 27 (1) 72–77 (1974).

Millipore advertisement for Pellicon™ XL and Labscale™ TFF System (1997).

Millpore Pharmaceutical Process Filtration Catalogue (1995/1996).

Huyghe, et al., Human Gene Therapy, vol. 6, pp. 1403–1416 (1995).

\* cited by examiner

COMPOSTIONS COMPRISING VIRUSES AND METHODS FOR CONCENTRATING VIRUS PREPARATIONS

This application claims priority under 35 U.S.C. 119 to U.S. provisional application No. 60/074,873 filed Feb. 17, 1998 and No. 60/085,559 filed May 15, 1998. This application also is a continuation-in-part and claims priority under 35 U S.C. 120 to U.S. patent application Ser. No. 08/989,227 filed Dec. 11, 1997 now U.S. Pat. No. 6,261,823, which claims the benefit of U.S. provisional application No. 60/033,176 filed Dec. 13, 1996.

FIELD OF THE INVENTION

The present invention relates to compositions comprising viruses, especially viral vectors, having significantly improved stability. The compositions of the present invention are useful in maintaining the stability of viruses during storage, and virus-containing compositions of the present invention are particularly useful for therapeutic uses such as gene therapy. New methods for concentrating and purifying virus preparations are also provided.

BACKGROUND

Viruses have become increasingly important for therapeutic uses, such as vaccinations and gene therapy, and there is a need to develop and prepare stable virus-containing compositions that can easily be stored and transported, yet retain sufficient safety and efficacy. In particular, given the extensive use of viral vectors in gene therapy, it is important to develop and prepare formulations that can stably preserve live recombinant viruses when they carry therapeutic transgenes.

Moreover, there is a critical need for formulations that can stabilize viral preparations at temperatures above −80° C. for extended periods of time. Virus-containing compositions normally require storage at −80° C. and cannot be stored at standard refrigeration temperatures (e.g., 2° C. to 8° C., or higher) for substantial periods of time. This limitation represents a serious impediment not only to storage, but also to processing, distribution, and widespread clinical use.

There is also a need to develop virus-containing compositions that can maintain pH in the range of about 7 to about 8.5 for extended periods despite being exposed to refrigeration temperatures, and despite being subjected to harsh conditions such as freeze/thaw, especially the slow rates of freeze/thaw that can occur in connection with larger scale production, handling, or distribution. Maintenance of pH is important for viral preparations because at pH below 7.0 and above 8.5 the live virus particles are vulnerable to losing viability due to physical and biological instability.

Additional problems relate to increasing virus concentrations. In particular, high virus concentration contributes significantly to virus instability. However, increasingly higher concentrations of virus and viral vectors are required for therapeutic use. Therefore, there is a critical need to develop formulations that stabilize relatively high concentrations of virus, especially under the harsh conditions mentioned above. And in addition, there is a particular need to develop new methods of concentrating an existing virus preparation to achieve stable preparations at higher concentration levels. The problems of instability associated with higher virus concentrations are exacerbated significantly if one tries to concentrate an existing virus preparation. This is in part due to the additional mechanical shear forces that come to bear during efforts to increase the concentration of an existing virus preparation. If one could find a method to concentrate a virus preparation without substantial impairment to virus stability, then clinical dosages at any desired concentration could be readily prepared (even when starting with material having a lower concentration) and, importantly, the ability to concentrate virus could eliminate problematic bottlenecks and other scale-up problems during the purification process by allowing significantly higher throughput during various processing steps such as size exclusion chromatography.

There is thus a need for materials and methods to accomplish the foregoing objectives.

SUMMARY OF INVENTION

The present invention fills the above-mentioned needs by providing a stable composition comprising virus in a formulation comprising a polyhydroxy hydrocarbon buffered to maintain a pH in a range from about 7 to about 8.5 at a temperature in the range from about 2° C. to 27° C.

Also provided are new methods of concentrating an existing virus preparation that allow one to readily select and prepare clinical dosages in a wide range of desired concentrations. A preferred method of concentrating a virus preparation comprises:

(a) adding a polyhydroxy hydrocarbon to a virus preparation to a final polyhydroxy hydrocarbon concentration of about 20% or more; and (b) subjecting the virus preparation to a filtration process wherein the concentration of virus is increased by applying pressure to the preparation such that diluent is removed from the virus preparation through a filter while the virus is retained.

Also provided herein is a method for concentrating a virus preparation comprising:

(a) centrifuging a composition which comprises a first layer comprising a polyhydroxy hydrocarbon in a concentration of 35% to 80% (v/v), the first layer overlaid with a second layer comprising a polyhydroxy hydrocarbon in a concentration of 5% to 30% (v/v), the second layer overlaid with a third layer comprising virus; and (b) recovering the virus from the first layer.

Furthermore, the present inventors found that their new method of increasing virus concentration has the additional advantage of enhancing further processing (e.g. by reducing or eliminating problematic bottlenecks during subsequent purification by allowing significantly higher throughput during processing steps such as size exclusion chromatography). Thus, in a preferred embodiment, the method of concentrating virus preparations in accordance with present invention further comprises a subsequent purification step (e.g., size exclusion chromatography). In this regard, the method of the present invention is particularly useful when a step of size exclusion chromatography is performed subsequent to ion exchange chromatography, and the virus preparation is concentrated (in accordance with the present invention) after the ion exchange chromatography but prior to the size exclusion chromatography. Viral fractions obtained from anion exchange chromatography, for example, typically contain high levels of salts and possibly other impurities that further compromise virus stability during concentration procedures. Thus, in a particularly preferred embodiment, the present invention provides a method of purifying a virus preparation comprising:

(a) subjecting the virus preparation to anion-exchange chromatography, wherein the virus is eluted as a virus preparation product from an anion-exchange chromatographic medium;

(b) adding a polyhydroxy hydrocarbon to the virus preparation product of step (a) so that the concentration of polyhydroxy hydrocarbon in the preparation reaches a final concentration of about 25% or more; and (c) increasing the concentration of virus in the virus preparation product of step (b) by applying pressure to the preparation such that diluent is removed from the virus preparation through a filter while the virus is retained; and (d) subjecting the concentrated virus preparation product of step (c) to one or more additional processing steps.

The present invention also provides virus preparations concentrated and/or purified by the foregoing methods.

DETAILED DESCRIPTION

As noted above, the present application discloses novel virus-containing compositions, as well as novel methods of concentrating and purifying virus-containing compositions.

With regard to compositions, the present inventors have developed a novel buffered formulation that can preserve viral preparations with enhanced stability. In particular, the formulation can stabilize viral preparations at temperatures well above −80° C. More important still, the compositions of the present invention are stable at typical refrigeration temperatures of, e.g., 2° to 8° C., or higher, for substantial periods of time, preferably for several months or more. This is a critical advantage because, as mentioned above, in order to meet clinical needs it is impractical to keep viral preparations frozen at −80° C. during storage and transportation.

An important feature of the compositions of the present invention is the addition of a polyhydroxy hydrocarbon. As used herein, a polyhydroxy hydrocarbon means a branched, linear, or cyclic compound substituted with 2 or more (preferably 2 to 6, more preferably 2 to 4) hydroxy groups. Polyhydroxy hydrocarbons for use in the present invention preferably are polyhydroxy-substituted alkyl compounds (branched or unbranched), preferably having 2 to 7 carbon atoms, and can include, e.g., glycerol, sorbitol and polypropanol. Glycerol is particularly preferred. As shown by data provided below, the present inventors found that glycerol allows for surprisingly high levels of stability for extended periods of time even under standard refrigeration conditions.

An effective amount of polyhydroxy hydrocarbon for compositions of the present invention is an amount sufficient to stabilize the virus in the formulation of the present invention without adversely affecting the effectiveness of the virus for further use, especially in cases where the virus contains a transgene for use in gene therapy. The polyhydroxy hydrocarbon is preferably present at a final concentration of about 20 to 200 mg/mL. A narrower range can be 80 to 120 mg/mL. More than one polyhydroxy hydrocarbon can be used to achieve the desired total amount of polyhydroxy hydrocarbon in the composition of the present invention.

The polyhydroxy hydrocarbon in compositions of the present invention can optionally contain an aldehyde group. In particular, the polyhydroxy hydrocarbon can be a disaccharide such as sucrose. Furthermore, even if the polyhydroxy hydrocarbon selected for the composition does not contain an aldehyde group, the composition can additionally include a disaccharide, such as sucrose, as a stabilizer and tonicity-adjusting agent. When the composition of the present invention already contains a suitable polyhydroxy hydrocarbon (such as glycerol) and a disaccharide is employed in preferred embodiments as an additional stabilizer or tonicity-adjusting agent, the disaccharide is preferably present in a range of 5 to 25 mg/mL, more preferably 20 mg/mL, and preferably the disaccharide is sucrose.

Pharmaceutically acceptable divalent metal salt stabilizers, such as magnesium salts, zinc salts and calcium salts, are used in preferred embodiments of the composition of the present invention. Preferably, the salt is a chloride salt or a magnesium salt, magnesium salt being particularly preferred. Preferably, the salt (e.g., the magnesium salt) is present in an amount of from about 0.1 to 1 mg/mL, more preferably in an amount of about 0.4 mg/mL.

Pharmaceutically acceptable monovalent metal salt stabilizers such as potassium, sodium, lithium and cesium salts may be included in preferred embodiments of the present invention as optional stabilizers. Preferably, the salt is sodium chloride present in the amount of 0.6 to 10.0 mg/ml, more preferably in an amount of about 5.8 mg/ml.

In addition to stabilizing the composition, sodium chloride may suppress the rate and extent of the appearance of by-products of fermentation, resulting in a more pharmaceutically elegant presentation that may have reduced antigenicity potential due to protein aggregates. The addition of sodium chloride does not affect the pH of the formulation.

The composition of the present invention is capable of maintaining a pH in the range of about 7 to about 8.5 for extended periods of time, even when subjected to harsh conditions such as refrigeration and freeze/thaw. Moreover, the compositions can remain stable and maintain the required pH range even when subjected to the relatively slow rate of freeze/thaw that can occur in connection with larger scale production, distribution, and handling. As noted above, maintenance of pH is important for viral preparations, because at pH below 7.0 and above 8.5 the live virus particles can become unstable and degrade. The particular composition of viruses makes viruses difficult to stabilize and preserve.

To accomplish pH maintenance under harsh conditions, the present invention preferably comprises a buffer system that can maintain an optimal pH in a range from about 7.0 to about 8.5 despite storage between −80° C. and 27° C. and despite being subjected to freeze/thaw conditions. Since pH can vary depending on temperature, pH ranges of the present invention are more specifically illustrated below with reference to specific temperature ranges. For instance, at refrigeration temperatures (e.g., about 2° C. to 8° C.) a preferred pH range is about 7.7 to about 8.3, more preferably about 7.9 to about 8.2. At room temperature (e.g., about 20° C. to 27° C., preferably 22° C.–25° C.), a preferred pH range is about 7.3 to about 8.2, more preferably about 7.4 to about 7.9.

A preferred buffer system of the present invention comprises sodium phosphate monobasic dihydrate in a concentration of about 0.5 to 10 mg/mL and tromethamine in a concentration of about 0.5 to 10 mg/mL. (Tromethamine is also known as TRIS or "Trizma" available from Sigma Chemical Co.). However, other buffer systems can be used. For example, sodium phosphate dibasic dihydrate can be used if coupled with an acidic form of tris buffer. In a particularly preferred embodiment, the buffer system comprises sodium phosphate monobasic dihydrate in a concentration of about 1.7 mg/mL and tromethamine in a concentration of about 1.7 mg/mL, and has the ability to maintain the formulation in an optimal pH range of about 7.3 to about 7.9 at 25° C.

The formulation of the present invention has the additional advantage of having the ability to stabilize high concentrations of virus at the above-mentioned harsh conditions (such as refrigeration temperatures and freeze/thaw processing). In particular, the formulation of the present invention can maintain stability of the virus at concentrations ranging up to $1 \times 10^{13}$ particles/mL. A preferable range of virus concentrations for use in the present invention is in an amount of $1 \times 10^9$ to $1 \times 10^{13}$ particles/mL., more preferably, up to $1 \times 10^{12}$ particles/mL, e.g. $1 \times 10^9$ (or $1 \times 10^{10}$) to $1 \times 10^{12}$.

The term "diluent" as used herein can comprise a solvent (e.g., water, preferably sterile water) or a mixture of a solvent and other ingredients such as additional solvents, additional stabilizers, additional buffers, and/or other substances that do not adversely affect safety, efficacy and stability of the formulation. With regard to diluents, stabilizers, buffers and the like, reference may be made, e.g., to Remington's Pharmaceutical Science, 15th Ed., Mack Publishing Company, Easton, Pa.

A surfactant, preferably a nonionic detergent such as a polyoxyethylene fatty acid ester (e.g., polyoxyethylenesorbitans such as Polysorbate 20, Polysorbate 40, Polysorbate 60, or Polysorbate 80 from ICI Americas, Inc., Wilmington Del., or Tween 20, Tween, 40, Tween 60 and Tween 80 from Sigma, St. Louis, Mo.), can optionally be included in the composition of the present invention. Preferably, the nonionic detergent is a polyoxyethylene fatty acid ester, and the polyoxyethylene fatty acid ester is preferably Polysorbate 80, which can act as a stabilizer in the composition of the present invention. The concentration of non-ionic detergent is preferably in a range of 0.03 to 0.3 mg/mL; more preferably, 0.15 mg/mL.

Compositions of the present invention can further contain one or more "delivery-enhancing agents". A "delivery-enhancing agent" refers to any agent which enhances delivery of a therapeutic gene, such as a tumor suppressor gene to a cancerous tissue or organ. Examples of such delivery-enhancing agents include but are not limited to detergents, alcohols, glycols, surfactants, bile salts, heparin antagonists, cyclooxygenase inhibitors, hypertonic salt solutions, and acetates.

Detergents (as the term is used herein) can include anionic, cationic, zwitterionic, and nonionic detergents. Exemplary detergents include but are not limited to taurocholate, deoxycholate, taurodeoxycholate, cetylpyridium, benalkonium chloride, ZWITITERGENT® 3-14 detergent, CHAPS (3-[3-Cholamidopropyl) dimethylammoniol]-1-propanesulfonate hydrate, Aldrich), Big CHAP, Deoxy Big CHAP, TRITON®-X-100 detergent, C12E8, Octyl-B-D-Glucopyranoside, PLURONIC®-F68 detergent, TWEEN® 20 detergent, and TWEEN® 80 detergent (CALBIOCHEM® Biochemicals).

The use of delivery-enhancing agents is described in detail in copending U.S. patent application Ser. No. 08/889, 335 filed on Jul. 8, 1997 (now abandoned), International Application Publication No. WO 97/25072, Jul. 17, 1997, in U.S. patent application Ser. No. 09/112,074 filed on Jul. 8, 1998 (currently pending), and International Application PCT/US 98/14241. In addition, use of calpain inhibitors in conjunction with viral vectors to increase transduction efficiency is described in U.S. patent application Ser. No. 09/172,685 filed on Oct. 15, 1998 (now abandoned) corresponding to International Application PCT/US 99/21453 filed on Oct. 14, 1999 (International Application Publication No. WO 00/21575), and No. 60/104321 filed on Oct. 15, 1998.

A wide range of viruses can be used in the compositions of the present invention, including but not limited to adenoviruses, pox viruses, iridoviruses, herpes viruses, papovaviruses, paramyxoviruses, orthomyxoviruses, retroviruses, adeno-associated virus, vaccinia virus, rotaviruses, etc. (see, e.g., Anderson, Science (1992) 256: 808–813); adenoviruses being particularly preferred. The viruses are preferably recombinant viruses, but can include clinical isolates, attenuated vaccine strains, and so on. Thus, for example, an exemplary recombinant adenovirus that can be used in compositions of the invention is A/C/N/53, which is disclosed in PCT patent application no. WO 95/11984.

The formulation of the present invention is particularly well suited for stabilizing a recombinant virus, such as a live recombinant adenovirus (or "viral vector"), for therapeutic use in gene therapy. For instance, the virus used in the present invention can comprise a tumor suppressor gene, such as a wild-type p53 gene or an Rb gene (e.g., $p110^{RB}$ or $p56^{RB}$), and with transgenes such as wild-type p53 inserted in a viral vector, the composition of the present invention can be used as a pharmaceutical composition for treatment of cancer.

In this regard, the formulations of the present invention have a remarkable ability to maintain the viability of live virus, in particular a viral vector into which a nucleotide sequence encoding a transgene such as p53 has been inserted. This feature allows the virus to maintain its ability to infect target cells so that the therapeutic protein encoded by the inserted transgene is adequately produced.

With specific regard to p53 and its uses, it is noted that mutation of the p53 gene is the most common genetic alteration in human cancers (Bartek (1991) Oncogene, 6: 1699–1703, Hollstein (1991) Science, 253: 49–53). Introduction of wild-type p53 in mammalian cancer cells lacking endogenous wild-type p53 protein suppresses the neoplastic phenotype of those cells (see, e.g., U.S. Pat. No. 5,532,220).

In the examples below, the virus is a live recombinant adenovirus containing wild-type p53 gene. The particular viral vector construct used in these examples is referred to herein as "A/C/N/53." A/C/N/53 (also referred to as "ACN53") is a particularly preferred viral vector construct described in U.S. Pat. No. 6,210,939 filed on Oct. 25, 1994, and in WO 95/11984 (May 4, 1995), expressly incorporated herein by reference.

A representative formula for preferred embodiments of the present invention that contain Polysorbate 80 is set forth below:

| Representative Formula | | |
|---|---|---|
| Active Substance | A/C/N/53 | $1 \times 10^9$ to $1 \times 10^{13}$ particles/mL |
| Buffer | Sodium Phosphate Monobasic | 0.5 to 10 mg/mL |
| | Tromethamine | 0.5 to 10 mg/mL |

-continued

Representative Formula

| | | |
|---|---|---|
| Stabilizer/tonicity agent | Sucrose | 5 to 25 mg/mL |
| Stabilizers | Glycerol | 20 to 200 mg/mL |
| | Magnesium Chloride | 0.1 to 1 mg/mL |
| | Polysorbate 80 | 0.03 to 0.3 mg/mL |
| Solvent | Water for Injection q.s. ad | 1 mL |

(The compositions are typically stored in 1.0 mL dosages. "q.s. ad" in the formula above means adding sufficient solvent to reach the 1 mL total volume).

Four particularly preferred embodiments are set forth below. (Polysorbate 80 is present in Examples 1 and 2, but absent in Examples 3 and 4).

| | Example 1 | Example 2 |
|---|---|---|
| A/C/N/53 | $7.5 \times 10^{11}$ particles/mL | $7.5 \times 10^{10}$ particles/mL |
| Sodium Phosphate Monobasic Dihydrate | 1.7 mg/mL | 1.7 mg/mL |
| Tromethamine | 1.7mg/mL | 1.7 mg/mL |
| Magnesium Chloride Hexahydrate | 0.4 mg/mL | 0.4 mg/mL |
| Sucrose | 20 mg/mL | 20 mg/mL |
| Polysorbate 80 | 0.15 mg/mL | 0.15 mg/mL |
| Glycerol | 100 mg/mL | 100 mg/mL |
| Water for Injection q.s. ad | 1 mL | 1 mL |
| pH | 7.4 to 7.8 | 7.4 to 7.8 |

| | Example 3 | Example 4 |
|---|---|---|
| A/C/N/53 | $7.5 \times 10^{11}$ particles/mL | $7.5 \times 10^{10}$ particles/mL |
| Sodium Phosphate Monobasic Dihydrate | 1.7 mg/mL | 1.7 mg/mL |
| Tromethamine | 1.7 mg/mL | 1.7 mg/mL |
| Magnesium Chloride Hexahydrate | 0.4 mg/mL | 0.4 mg/mL |
| Sucrose | 20 mg/mL | 20 mg/mL |
| Glycerol | 100 mg/mL | 100 mg/mL |
| Water for Injection q.s. ad | 1 mL | 1 mL |
| pH | 7.4 to 7.9 | 7.3 to 7.8 |

The following ingredients: sodium phosphate monobasic dihydrate, tromethamine, magnesium chloride hexahydrate, sucrose, and glycerol can all be obtained from, e.g., EM Industries, INC., 7 Skyline Drive, Hawthorne, N.Y. 10532. Polysorbate 80 is available from, e.g., ICI Americas, Inc., Wilmington Del., 19897.

Compositions of the present invention can be prepared during purification of the virus in a gel filtration chromatography column by combining the ingredients (excluding Polysorbate-80) at the desired concentrations in the gel filtration column. (With regard to gel filtration methods, reference can be made, e.g., to Section V below). Then, if it is desired to dilute the concentration of the virus, or to incorporate Polysorbate-80, then diluents can be prepared by standard techniques. An illustrative example is set forth below:

Charge and dissolve sodium phosphate monobasic dihydrate, tromethamine, sucrose, magnesium chloride hexahydrate and glycerol in approximately 75% of batch volume of water for injection at room temperature in a stainless steel vessel equipped with agitator. Bring the batch of the resulting diluent to final volume with water for injection. Check the pH. Calculate the required volume of A/C/N/53 (adenovirus with wild-type p53 as a transgene) Drug Substance in Suspension and the required volume of diluent to make A/C/N/53 Injection. If the final A/C/N/53 Injection will contain Polysorbate 80, prepare a stock solution that contains 10% excess Polysorbate 80 in diluent. Charge the calculated amounts of A/C/N/53 Drug Substance in Suspension and diluent into a stainless steel container and mix. Charge the Polysorbate 80 solution, prior to adding all of the Diluent, based upon 10% of the total A/C/N/53 Injection batch volume if required. Aseptically filter the suspension through a sterilized filter (0.22 μm or equivalent). Test the filter integrity after filtration. Collect and fill the sterilized suspension into vials having the appropriate volume. Stopper and seal the vials.

Stability data for Examples 1, 2, 3, and 4 are set forth, respectively, in Tables 1, 2, 3, and 4 below.

In the Tables below, the antiproliferation assay is a bioassay used to measure the product's ability to suppress cancer cells and is based generally on procedures used by Wills, et al., 1994, Human Gene Therapy, 5:1079–1088. The numbers listed indicate activity whereas the control has no activity.

The "Plaque Assay" measures virus particles in culture by scoring the number of viral plaques as a function of dilution and is based generally on procedures described in Graham, F. L., and Prevec, L., *Methods in Molecular Biology*, vol. 7: *Gene Transfer and Expression Protocols*, E. J. Murray, ed. (Humana Press Inc., Clifton N.J.) pp. 109–128 (1991); see also Graham, F. L., Smiley, J., Russel, W. C., and Nairn, R., *J. Gen. Virol.* vol. 36, pp 59–74 (1977).

The "FACS" assay shows the ability of the virus to infect cells, and these measurements are based generally on methods described in, e.g., International Patent Application PCT/US97/11865 (WO 98/01582, published Jan. 15, 1998). In the next column to the right, the numbers presented under the heading "Concentration" represent the concentration of the total number of virus particles. Finally, the numbers under the heading "Particle/FACS ratio" represent the ratio of the total number of virus particles as compared to the number of infectious virus particles, thus indicating the relative potency of the virus preparation.

The data under the heading "UV" indicate the aggregation of the virus particles as shown by the UV absorbance ratio for the wavelengths $A_{320}/A_{260}$ as an indication of light scatter. Basically, the absorbance at 320 nanometer wavelength measures the amount of light scatter, whereas the absorbance at 260 nanometer wavelength correlates with amount of DNA.

The temperatures listed in the second column of the tables under "condition" represent the storage temperature. The physiological assays are performed at 37° C. and the pH in the last column is measured at room temperature, approximately 25° C.

TABLE 1

Stability Data on Example 1

| Stability Time | Condition °C. | Antiproliferation Assay ×10⁵ SPU/mL | Plaque Assay ×10⁸ PFU/mL | FACS ×10¹⁰ U/mL | Concentration ×10¹¹ part./mL | Particles FACS Ratio | UV $A_{320}/A_{260}$ | pH |
|---|---|---|---|---|---|---|---|---|
| initial |  | 3.3 | 5.8 | 3.86 | 7.95 | 21 | 0.23 | 7.53 |
| 1 week | 25 | 4.9 | 10 | 2.27 | 8.06 | 36 | 0.24 | 7.53 |
| 2 weeks | 4 | 3.1 | 6.6 | 3.41 | 7.84 | 23 | 0.23 | 7.49 |
| 4 weeks | 4 | 3.4 | 17 | 3.91 | 7.79 | 20 | 0.23 | 7.63 |
| 8 weeks | 4 | 5.8 | 8.8 | 3.38 | 7.80 | 23 | 0.24 | 7.61 |
| 12 weeks | 4 | 3.9 | 36 | 2.24 | 7.80 | 35 | 0.24 | 7.72 |
| 5 months | 4 | not tested | not tested | 1.57 | 8.21 | 52 | 0.26 | 7.60 |
| 6 months | 4 | 3.0 | 7.6 | 2.74 | 7.68 | 28 | 0.28 | 7.58 |
| 9 months | 4 | 3.1 | 19 | 3.47 | 7.19* | 21 | 0.28 | 7.58 |
| 11 months | 4 | not tested | not tested | nt | 6.71 | — | 0.29 | nt |
| 12 months | 4 | 2.6 | 10 | 0.81 | 6.13 | 76 | 0.30 | 7.62 |

*Retest of 9 month UV samples: $6.89 \times 10^{11}$ particles/mL; $A_{320}/A_{260} = 0.28$.

TABLE 2

Stability Data on Example 2

| Stability Time | Condition °C. | Antiproliferation Assay ×10⁴ SPU/mL | Plaque Assay ×10⁷ PFU/mL | FACS ×10⁹ U/mL | Concentration ×10¹⁰ part./mL | Particles FACS Ratio | UV $A_{320}/A_{260}$ | pH |
|---|---|---|---|---|---|---|---|---|
| initial |  | 3.3 | 4.8 | 1.99 | 10.0 | 50 | 0.24 | 7.36 |
| 1 week | 25 | 2.4 | 7.1 | 1.64 | nd* | — | 0.46 | 7.42 |
| 2 weeks | 4 | 2.4 | 6.9 | 2.13 | 9.79 | 46 | 0.24 | 7.51 |
| 4 weeks | 4 | 3.2 | 8.4 | 2.50 | 9.24 | 37 | 0.22 | 7.55 |
| 8 weeks | 4 | 6.9 | 8.6 | 2.60 | 8.10 | 31 | 0.25 | 7.54 |
| 12 weeks | 4 | 5.5 | 8.3 | 1.09 | 8.60 | 79 | 0.24 | 7.64 |
| 5 months | 4 | not tested | not tested | 1.74 | 8.03 | 46 | 0.27 | 7.55 |
| 6 months | 4 | 3.3 | 7.3 | 2.10 | 8.25 | 39 | 0.23 | 7.52 |
| 9 months | 4 | 2.3 | 13 | 1.97 | 7.59 | 39 | 0.24** | 7.53 |
| 11 months | 4 | not tested (nt) | not tested | nt | 7.48 | — | 0.23 | nt |
| 12 months | 4 | 1.5 | 9.4 | 0.60 | 4.94 | 82 | 0.26 | 7.59 |

*Not determined due to assay interference.
**Retest of 9 month UV samples: $7.37 \times 10^{10}$ particles/mL; $A_{320}/A_{260} = 0.24$.

TABLE 3

Stability Data on Example 3

| Stability Time | Condition °C. | Antiproliferation Assay ×10⁵ SPU/mL | Plaque Assay ×10⁸ PFU/mL | FACS ×10¹⁰ U/mL | Concentration ×10¹¹ part./mL | Particles FACS Ratio | UV $A_{320}/A_{260}$ | pH |
|---|---|---|---|---|---|---|---|---|
| initial |  | 3.2 | 6.3 | 2.59 | 7.45 | 29 | 0.24 | 7.67 |
| 1 week | 25 | 4.4 | 4.3 | 1.65 | 7.49 | 45 | 0.24 | 7.68 |
| 2 weeks | 4 | 2.3 | 8.0 | 3.62 | 7.27 | 20 | 0.24 | 7.49 |
| 4 weeks | 4 | 2.7 | 7.6 | 4.08 | 6.97 | 17 | 0.24 | 7.75 |
| 8 weeks | 4 | 5.9 | 8.7 | 2.69 | 7.00 | 26 | 0.25 | 7.82 |
| 12 weeks | 4 | 3.0 | 15 | 0.70 | 7.10 | 101 | 0.25 | 7.80 |
| 6 months | 4 | 2.4 | 6.4 | 2.45 | 7.12 | 29 | 0.25 | 7.76 |
| 9 months | 4 | 2.8 | 9.4 | 2.51 | 7.06 | 28 | 0.26 | 7.81 |
| 11 months | 4 | not tested (nt) | nt | nt | 6.71 | — | 0.25 | nt |
| 12 months | 4 | 2.2 | 9.8 | 0.74 | 6.75 | 91 | 0.26 | 7.81 |

TABLE 4

Stability Data on Example 4

| Stability Time | Condition °C. | Antiproliferation Assay ×10$^4$ SPU/mL | Plaque Assay ×10$^7$ PFU/mL | FACS ×10$^9$ U/mL | Concentration ×10$^{10}$ part./mL | Particles FACS Ratio | UV A$_{320}$/A$_{260}$ | pH |
|---|---|---|---|---|---|---|---|---|
| initial |  | 3.3 | 4.7 | 2.36 | 8.91 | 38 | 0.23 | 7.37 |
| 1 week | 25 | 2.3 | 9.3 | 1.40 | 8.25 | 59 | 0.24 | 7.37 |
| 2 weeks | 4 | 2.8 | 8.0 | 2.16 | 8.80 | 41 | nd* | 7.37 |
| 4 weeks | 4 | 2.9 | 6.6 | 2.54 | 9.35 | 37 | 0.20 | 7.63 |
| 8 weeks | 4 | 6.9 | 7.2 | 2.56 | 7.60 | 30 | 0.24 | 7.60 |
| 12 weeks | 4 | 4.4 | 8.6 | 1.45 | 7.20 | 50 | 0.23 | 7.73 |
| 6 months | 4 | 3.6 | 7.1 | 2.85 | 7.92 | 28 | 0.21 | 7.58 |
| 9 months | 4 | 2.9 | 11 | 1.87 | 7.26 | 39 | 0.20 | 7.60 |
| 11 months | 4 | not tested (nt) | nt | nt | 6.93 | — | 0.22 | nt |
| 12 months | 4 | 2.4 | 22 | 0.70 | 7.15 | 102 | 0.23 | 7.61 |

*Not determined due to assay interference.

EXAMPLE 5

Formulation for Example 5: A/C/N/53 (7.5×10$^{11}$ Particles/mL), Tromethamine (TRIS) (1.7 mg/mL), Sodium Phosphate Monobasic Dihydrate (1.7 mg/mL), Sucrose (20 mg/mL), Magnesium Chloride Hexahydrate (0.4 mg/mL), Glycerol (100 mg/mL), Sodium Chloride (5.8 mg/mL), Fill Volume=10 mL.

TABLE 5

Stability Data on Example 5

| Stability Time | Condition °C. | Antiproliferation Assay ×10$^5$ SPU/mL | FACS ×10$^{10}$ U/mL | Concentration ×10$^{11}$ part./mL | Particles FACS Ratio | UV A$_{320}$/A$_{260}$ | pH |
|---|---|---|---|---|---|---|---|
| initial |  | 4.5 | 1.87 | 7.81 | 42 | 0.23 | 7.80 |
| 1 month | 4 | 8.0 | 1.67 | 7.83 | 47 | 0.23 | 7.80 |
| 4 month | 4 | 13.0 | 1.58 | 7.84 | 50 | 0.23 | 7.70 |

In some cases, particulates have been observed to form in the formulation during storage at 4° C. Analysis of the particulates by SDS-PAGE suggests that the particulates are composed of minor impurities (i.e., additional proteins and some immature viral particles), and thus these particulates do not affect the viability of the formulation. Nonetheless, in a preferred embodiment to further clarify the formulation (to prevent possible particulate formation), an optional step of microfiltration can be carried out to remove any potential particulates with little loss of viral particles. (When carrying out microfiltration, it should be noted that sufficient microfiltration membrane surface area per filtration volume is critical to avoid loss of virus as the particulate is removed.)

In addition, in a preferred embodiment, the present inventors have found that agitation, such as stirring, can accelerate particulate formation and is therefore an additional optional step in the clarification process. Thus, gentle stirring (e.g., overnight, 10° C., using a magnetic stirbar) followed by microfiltration was shown to remove the particulates such that no more particulate would reform upon restirring.

It was also found that cycles of freeze/thaw could promote particulate formation during restirring. Thus, in another preferred procedure, one or more freeze/thaw cycles can optionally be carried out, followed by stirring, and then microfiltration, for the prevention of particulate formation during storage of the virus final product at refrigeration temperatures (e.g. 4° C.).

Methods of Concentrating and Purifying Virus-Containing Compositions

The present application also discloses a new method of stably concentrating an existing virus preparation by employing tangential flow filtration (hereafter sometimes referred to as "TFF"), allowing one to readily select and prepare clinical dosages in a wide range of desired concentrations. The new method of concentrating a virus preparation comprises:

(a) adding a polyhydroxy hydrocarbon to a virus preparation to a final polyhydroxy hydrocarbon concentration of about 20% or more; and (b) subjecting the virus preparation to a filtration process wherein the concentration of virus is increased by applying pressure to the preparation such that diluent is removed from the virus preparation through a filter while the virus is retained.

The methods of the instant invention are amenable to a wide range of viruses, including but not limited to adenoviruses, pox viruses, iridoviruses, herpes viruses, papovaviruses, paramyxoviruses, orthomyxoviruses, retroviruses, adeno-associated virus, vaccinia virus, rotaviruses, etc.; adenoviruses being particularly preferred. The viruses are preferably recombinant viruses, but can include clinical isolates, attenuated vaccine strains, and so on. The present invention is particularly useful for concentrating recombinant viruses carrying a heterologous transgene for use in gene therapy. Such viruses are especially vulnerable to potentially destabilizing forces, such as the additional shear mechanical forces accompanying methods of concentrating virus preparations. An exemplary recombinant adenovirus that can be concentrated by the method of the invention is A/C/N/53, which is disclosed in PCT Patent Application No. WO 95/11984.

The filtration process used to concentrate the virus according to the method of the present invention can include any filtration process (e.g., ultrafiltration) where the concentration of virus is increased by forcing diluent to be passed through a filter in such a manner that the diluent is removed from the virus preparation whereas the virus is unable to pass through the filter and thereby remains, in concentrated form, in the virus preparation. Ultrafiltration is described in detail in, e.g., *Microfiltration and Ultrafiltration: Principles and Applications,* L. Zeman and A. Zydney (Marcel Dekkar, Inc., New York, N.Y., 1996). A particularly preferred filtration process is Tangential Flow Filtration ("TFF") as described in, e.g., MILLEPORE catalogue entitled "Pharmaceutical Process Filtration Catalogue" pp. 177–202 (Bedford, Mass., 1995/96). Preferred TFF apparatus comprises either a Pellicon II or Pellicon XL filter system from Millipore Corporation, 80 Ashby Rd., Bedford, Mass. (internet address: www.millipore.com), a Pellicon XL system being particularly preferred. In a preferred embodiment, the methods of the present invention are carried out at temperatures in a range from about 2° C. to 27° C.

Other concentration processes can be employed to concentrate virus preparations in accordance with the present invention. For instance, employment of polyhydroxy hydrocarbon can advantageously be used to concentrate a virus preparation by centrifugation. Thus, the present invention also provides a method for concentrating a virus preparation comprising:

(a) centrifuging a composition which comprises a first layer comprising a polyhydroxy hydrocarbon in a concentration of 35% to 80% (v/v), the first layer overlaid with a second layer comprising a polyhydroxy hydrocarbon in a concentration of 5% to 30% (v/v), the second layer overlaid with a third layer comprising virus; and (b) recovering the virus from the first layer.

By way of example, an adenovirus preparation can be concentrated by low speed centrifugation at 3,200 g using swing bucket rotors of a Beckman centrifuge. To accomplish this, the virus preparation can be placed into multiple 5 ml tubes, each tube containing 6.25% volume of 70% glycerol in a first layer at the tube bottom, overlaid with 2.5% volume of 20% glycerol, with the virus preparation laid on top. The preparation is then centrifuged at 3,200 g at 4° C. for approximately 16 hours to pellet the newly-concentrated virus into the glycerol layers and then the newly-concentrated virus preparation is subsequently recovered from the first layer. Virus concentrated by the procedures described above had good light scattering characteristics and had suitable infectivity properties.

With regard to the polyhydroxy hydrocarbon used in the methods of the present invention, a "polyhydroxy hydrocarbon" means a branched, linear, or cyclic compound substituted with 2 or more (preferably 2 to 6, more preferably 2 to 4) hydroxy groups, and an effective amount of polyhydroxy hydrocarbon is an amount sufficient to stabilize the virus against potentially destabilizing forces, such as the mechanical shear forces that occur during the concentration process. Preferably, the polyhydroxy hydrocarbon in the virus-concentrating methods of the present invention is present in a minimum concentration of 20%, more preferably 25%. Polyhydroxy hydrocarbons for use in the present invention preferably are polyhydroxy-substituted alkyl compounds (branched or unbranched), preferably having 2 to 7 carbon atoms, and can include glycerol, sorbitol and polypropanol. Glycerol is particularly preferred.

The inventors' new method of increasing virus concentration has the additional advantage of enhancing processing, e.g., by eliminating problematic bottlenecks by allowing significantly higher throughput during various processing steps such as size exclusion chromatography. Thus, in a preferred embodiment, the method of concentrating virus preparations in accordance with present invention can be applied to methods of purifying viruses where a size exclusion chromatography step (e.g., gel filtration) is performed subsequent to anion exchange chromatography. In this embodiment, there are additional threats to virus stability stenmming not only from the mechanical shear forces needed to concentrate the virus prior to the rate-limiting size exclusion chromatography step, but also due to the fact that the virus preparation eluted from the anion exchange chromatography step typically contains high levels of salts and other impurities that further compromise virus stability. Thus, in a particularly preferred embodiment, the present invention provides a method of purifying a virus preparation comprising:

(a) subjecting the virus preparation to anion-exchange chromatography, wherein the virus is eluted as a virus preparation product from an anion-exchange chromatographic medium;

(b) adding a polyhydroxy hydrocarbon to the virus preparation product of step (a) so that the concentration of polyhydroxy hydrocarbon in the preparation reaches a final concentration of about 25% or more; and (c) increasing the concentration of virus in the virus preparation product of step (b) by applying pressure to the preparation such that diluent is removed from the virus preparation through a filter while the virus is retained; and (d) subjecting the concentrated virus preparation product of step (c) to one or more additional processing steps.

In the preferred embodiment set forth above in connection with anion exchange chromatography, the minimum level of glycerol is 25% (rather than the 20% minimum level in general applications of the concentration methods of the present invention) because this particular application must take into account the additional threat to stability posed by the high salt concentrations in the product eluted from the anion exchange column. The addition of 25% glycerol (preferably 30%) results in stability of the salt-containing DEAE pool for >10 days at, e.g., 4° C.; therefore subsequent steps of virus concentration and/or gel filtration can be performed on separate days with substantial flexibility across a 10 day period. As will be appreciated, the employment of polyhydroxy hydrocarbon in the higher concentration of 25% or more can also be used in methods of the present invention when the virus preparation contains high salt content due to other processing conditions.

EXAMPLES OF METHODS OF THE PRESENT INVENTION

The following examples illustrate preferred embodiments of the present invention; the scope of the invention is not to be construed as limited thereby.

Brief Overview—A concentrated batch starts with frozen crude viral materials originating from fermentation recovery. In one embodiment, the adenovirus product is first purified by anion exchange chromatography. Then, prior to loading the preparation onto a size exclusion column, the anion exchange pool can be concentrated by tangential flow filtration (TFF) in the presence of 30% (v/v) glycerol. Alternatively, in another embodiment, the TFF concentration step can be carried out in the presence of 20% (v/v) or more (preferably 25%) glycerol after size exclusion chromatography.

Preparation of Starting Materials by Anion-Exchange Chromatography Prior to TFF

In a preferred embodiment, an adenovirus anion exchange pool is prepared for concentration as follows. Frozen viral material from fermentation and recovery steps is thawed and filtered through a 0.45 μm hydrophilic membrane. The salt concentration of the filtrate is adjusted by adding 4M sodium chloride. This feed solution is then applied to a Fractogel EMD DEAE-650M column pre-equilibrated with 50 mM sodium phosphate pH 7.5, 260 mM sodium chloride, 2 mM magnesium chloride, 2% (w/v) sucrose (Buffer A). The adenovirus binds to the anion exchange resin, whereas the majority of media and host cell impurities pass through the column ending up in the spent charge. The column is initially washed with 4 volumes of buffer A followed by a second isocratic wash of 8 bed volumes of 94% buffer A and 6% buffer B (50 mM sodium phosphate pH 7.5, 600 mM sodium chloride, 2 mM magnesium chloride, 2% (w/v) sucrose) to remove additional impurities. The virus is eluted from the column with a 30 bed volume linear gradient from 6% to 100% buffer B. The Adenovirus peak of the elution profile as determined by $A_{280}$ is collected. Then glycerol is added to the DEAE pool at a final concentration of 30% (v/v) for further processing.

Concentration of DEAE Pool Using Tangential Flow Filtration

The DEAE pool (prepared in accordance with the above description) is concentrated to 10- to 20-fold by using a Millipore TFF unit (Pellicon XL System) with 1 million molecular weight cut-off Biomax membranes. The process is carried out either at 2–10° C. or room temperature (25° C.). The following filtration parameters are used in this procedure: average inlet pressure=14 psi; average permeate pressure=o psi; average flux rate=13 liters/hour-square meter. The final concentration of adenovirus achieves approximately $1.0$–$2.0 \times 10^{13}$ particles per ml. Based on the Resource Q-HPLC and UV absorbance ($A_{260}$) analysis, the recovery of concentration step is >80% with no significant aggregation (light scattering assay by $A_{320}/A_{260}$).

Buffer Exchange by Size Exclusion Chromatography (Gel Filtration)

The concentrated adenovirus preparation is applied to a Superdex-200 size exclusion column pre-equilibrated with 20 mM sodium phosphate pH 8.0, 100 mM sodium chloride, 2 mM magnesium chloride, 2% (w/v) sucrose, 10% glycerol (Buffer C) or 11 mM sodium phosphate, 14 mM Tris, 2 mM magnesium chloride, 2% (w/v) sucrose, 10% glycerol, pH 7.8 (Buffer D). The column is eluted with equilibration buffer. The Adenovirus peak of the elution profile as determined by $A_{280}$ is collected and pooled. The concentrated adenovirus preparation is filtered through a 0.2 μm hydrophilic Durapore membrane (Stericup, Millipore) at 2 to 10° C., and can be stored at –80° C., or at higher temperatures (such as 2 to 100° C.).

Concentration of Superdex-200 Pool Using Tangential Flow Filtration

As discussed above, a preferred embodiment of the present invention involves concentrating the virus after anion exchange chromatography, but before gel filtration. However, in another embodiment, the disclosed methods of concentrating virus preparations can also be used after the gel filtration step (even if no virus concentration step was employed in between the anion exchange step and the gel filtration step). In this case, the filtration parameters are the same as those for concentration of a DEAE pool, except that the polyhydroxy hydrocarbon (e.g., glycerol) can be added to the Superdex-200 pool at a final concentration as low as 20% (v/v) since it is no longer necessary to deal with the high salt concentrations in the DEAE pool. In this regard, it should be noted that in cases where the addition of polyhydroxy hydrocarbon is postponed until after gel filtration, the DEAE pool should be applied immediately to the gel filtration column (due to the vulnerability of the DEAE pool—with its high salt concentration). Thus, it can be seen that an additional advantage of adding polyhydroxy hydrocarbon to the DEAE pool (in accordance with the present invention) is increased flexibility in terms of the time interval and storage options during the period of time between anion-exchange chromatography and subsequent processing.

The methods of concentrating virus preparations can be applied in connection with a variety of purification methods. For additional information on purification methods, reference can be made, e.g., to Huyghe et al., *Human Gene Therapy*, Vol. 6, pp. 1403–1416 (1995) and U.S. Pat. No. 6,261,823, expressly incorporated herein by reference.

Stability Data for Methods of Concentrating Virus Preparations Using Tangential Flow Filtration As shown by the experimental data below, the methods of the present invention allow for greatly enhanced virus stability, despite the mechanical shear forces of concentrating the virus, and despite harsh conditions such as high salt levels in a DEAE pool. Thus, methods of the present invention allow for, inter alia, (1) ready preparation of clinical dosages at any desired concentration (even when starting with material having a lower concentration), (2) enhancement of processing (e.g., by allowing significantly higher throughput during size exclusion chromatography), and (3) stability of the salt-containing DEAE pool for >10 days at 2–10° C. (thus allowing for subsequent steps of virus concentration and/or gel filtration to be performed on separate days with substantial flexibility across a 10 day period.

A. Concentrating Virus Subsequent to DEAE Chromatography

In the following three examples, stable concentrations of adenovirus were prepared by concentrating DEAE Pools in 30% glycerol (in accordance with the methods of the present invention). The preparations were then subjected to further purification by Superdex-200 gel filtration chromatography to obtain the final formulation for testing.

Example D-1

Final Formulation: 20 mM NaPi, 100 mM NaCl, 2 mM $MgCl_2$, 2% sucrose, 10% glycerol, pH 8 at 2–10° C.
Results: Particles/FACS=24 Light Scattering (A320/A260)= 0.22 Conc.=$1.6 \times 10^{13}$ particles/ml Example D-2

Final Formulation: 14 mM Tris base, 11 mM NaPi, 2 mM $MgCl_2$, 2% sucrose, 10% glycerol, pH 7.8 at 2–10° C.
Results: Particles/FACS=17 Light Scattering (A320/A260)= 0.25 Conc.=$1.5 \times 10^{13}$ particles/ml Example D-3

Final Formulation: 20 mM NaPi, 100 mM NaCl, 2 mM $MgCl_2$, 2% sucrose, 10% glycerol, pH 8 at 2–10° C.
Results: Particles/FACS=24 Light Scattering (A320/A260)= 0.25 Conc.=$1.3 \times 10^{13}$ particles/ml.

B. Concentrating Virus Subsequent to Gel Filtration

Example S-1

In the following example, the virus preparation was concentrated in 20% glycerol subsequent to gel filtration.

Final Formulation: 16 mM NaPi, 80 mM NaCl, 1.6 mM MgCl$_2$, 1.6% sucrose, 20% glycerol, pH 8 at 2–10° C.

Results: Particles/FACS=72; Light Scattering (A320/A260)=0.26 Conc.=1.66×10$^{13}$ particles/ml All publications, patents and patent applications cited herein are incorporated in their entirety by reference to the same extent as if each individual publication, patent or patent application was specifically and individually indicated to be incorporated by reference.

Modifications and variations of this invention will be apparent to those skilled in the art. The specific embodiments described herein are offered by way of example only, and the invention is not to be construed as limited thereby.

What is claimed is:

1. A composition comprising a recombinant adenovirus, 20 to 200 mg/ml glycerol, and an aqueous buffer system which maintains a pH range from about 7 to about 8.5 at a temperature range from about 2° C. to 27° C., wherein the recombinant adenovirus comprises a wild-type p53 gene.

2. The composition of claim 1 wherein the recombinant adenovirus is A/C/N/53.

3. The composition of claim 2 which further comprises sucrose and a divalent metal salt, and wherein the aqueous buffer system comprises sodium phosphate monobasic dihydrate and tromethamine and maintains a pH range from about 7.3 to about 7.9.

4. A composition comprising adenovirus, 20 to 200 mg/ml glycerol, sucrose, and an aqueous buffer system which maintains a pH range from about 7 to about 8.5 at a temperature range from about 2° C. to 27° C.

5. A composition comprising from 1×10$^9$ to 1×10$^{13}$ particles of A/C/N/53, 20 to 200 mg/ml glycerol, 5 to 25 mg/ml sucrose, a divalent metal salt, and an aqueous buffer system which comprises from 0.5 to 10 mg/ml sodium phosphate monobasic dihydrate and from 0.5 to 10 mg/ml tromethamine and which maintains a pH range from 7.3 to 8 at a temperature range from 4° C. to 27° C.

* * * * *